(12) United States Patent
Wallrafen

(10) Patent No.: US 6,356,087 B1
(45) Date of Patent: Mar. 12, 2002

(54) SYSTEM FOR DETERMINING RELATIVE AIR HUMIDITY

(75) Inventor: Werner Wallrafen, Bundesrepublik (DE)

(73) Assignee: Mannesmann VDO AG, Frankfurt am Main (DE)

( * ) Notice: Subject to any disclaimer, the term of this patent is extended or adjusted under 35 U.S.C. 154(b) by 0 days.

(21) Appl. No.: 09/462,538

(22) PCT Filed: Jun. 19, 1999

(86) PCT No.: PCT/EP98/03752

§ 371 Date: Apr. 27, 2000

§ 102(e) Date: Apr. 27, 2000

(87) PCT Pub. No.: WO99/02980

PCT Pub. Date: Jan. 21, 1999

(30) Foreign Application Priority Data

Jul. 11, 1997  (DE) .......................................... 197 29 697

(51) Int. Cl.[7] ................................................ G01R 27/26
(52) U.S. Cl. ........................................ 324/664; 324/689
(58) Field of Search ................................. 324/664, 678, 324/694, 696, 689; 73/335.04, 335.02

(56) References Cited

U.S. PATENT DOCUMENTS

| | | | |
|---|---|---|---|
| 4,603,372 A | 7/1986 | Abadie et al. | 361/286 |
| 5,296,819 A | 3/1994 | Kuroiwa et al. | 324/670 |
| 5,814,726 A * | 9/1998 | Mitter | 324/664 |

FOREIGN PATENT DOCUMENTS

| | | |
|---|---|---|
| DE | 3911812 | 10/1990 |
| DE | 4035371 | 5/1992 |
| DE | 19601592 | 1/1996 |
| GB | 2011093 | 11/1978 |
| GB | 2047431 | 3/1980 |

* cited by examiner

Primary Examiner—Safet Metjahic
Assistant Examiner—James Kerveros
(74) Attorney, Agent, or Firm—Mayer, Brown & Platt

(57) ABSTRACT

An arrangement for determining relative atmospheric humidity and temperature by means of a capacitive atmospheric humidity sensor and associated sensor evaluation electronics. The capacitive atmospheric humidity sensor has a polymer layer as a dielectric and two electrically conductive electrodes. For the temporary heating up of the capacitive atmospheric humidity sensor, one of the electrically conductive electrodes is designed as a laminar heating resistor with at least two power terminals.

11 Claims, 2 Drawing Sheets

SYSTEM FOR DETERMINING RELATIVE AIR HUMIDITY

This application is made pursuant to 35 U.S.C. §371 of international application number PCT/EP 98/03752, filed Jun. 19, 1998, with a priority date of Jul. 11, 1997.

FIELD OF THE INVENTION

The invention concerns an arrangement for determining relative atmospheric humidity by means of a capacitive atmospheric humidity sensor and associated sensor evaluation electronics, the capacitive atmospheric humidity sensor having a polymer layer as a dielectric and two electrically conductive electrodes.

BACKGROUND OF THE INVENTION

Such an arrangement is known, for example, from DE 28 51 686, the dielectric properties of this polymer layer representing a function of the relative atmospheric humidity. The determination of the relative atmospheric humidity in this case takes place by measuring the capacitance between the two electrically conductive electrodes. An improvement in the speed and accuracy of the measurement, in particular when there is high relative humidity, is to be achieved in this case by heating up the polymer layer.

In the case of such capacitive atmospheric humidity sensors, it has been found that the polymer layers become contaminated by foreign substances in the course of the service life. In particular when there is frequent condensation (that means an atmospheric humidity of approximately 100%), and when it is cold, residues remain in the layer, so that the functional interrelationship between capacitance and atmospheric humidity is disturbed. Long-term instabilities or signal drift are thus the consequence. If these sensor elements are then heated up, for example dried out in an oven, it is also possible for the measured values to be stabilized again, with the foreign substances also being eliminated.

If these atmospheric humidity sensors are used for air-conditioning systems in buildings, they are usually serviced or replaced regularly. If, however, the atmospheric humidity sensors are used in air-conditioning systems of motor vehicles, they must operate under aggravated conditions without servicing, if possible over a period of years.

Thus there is a need for an arrangement for determining relative atmospheric humidity of the type stated at the beginning which operates satisfactorily without any additional servicing effort.

Other needs will become apparent upon a further reading of the following detailed description taken in conjunction with the drawings.

SUMMARY OF THE INVENTION

The aforementioned needs are fulfilled according to the invention by one of the electrically conductive, metallized electrodes being designed as a laminar heating resistor with at least two power terminals.

The arrangement according to the invention has the advantage that the capacitive atmospheric humidity sensor can be heated up outside the measuring periods in a simple way and at any time, so that any contaminations there may be can be removed by vaporization.

In the case of the arrangement according to the invention, it may be provided that the electrically conductive electrodes are arranged on both sides of the polymer layer, opposite one another, or on one side of the polymer layer, alongside one another.

It is particularly advantageous if the electrodes of the capacitive atmospheric humidity sensor consist of platinum, which has a relatively high resistivity and, in the form of a thin foil, is consequently particularly suited as a heating resistor. In principle, some other noble metal can also be used.

In the case of the preferred exemplary embodiment, it is therefore possible to make the foil layer thickness of the platinum electrodes so small that moisture can penetrate through.

For the heating up of the capacitive atmospheric humidity sensor, the platinum electrode designed as a heating resistor is supplied with current in specific time cycles, it having been found to be advantageous if this takes place each time that the arrangement is switched on.

In the case of another embodiment of the invention, it is proposed that the heating resistor is supplied with current for a short time only when the ambient temperature is below a fixed predetermined value when the device is switched on. Provided here for sensing the ambient temperature is a temperature sensor which is connected to the sensor evaluation electronics and emits an appropriate compensating variable for determining the exact relative atmospheric humidity by the sensor evaluation electronics.

A development of the invention is that the heating resistor is in each case supplied with current only after a fixed predetermined waiting time, which has proven to be particularly cost-effective and cost-saving.

Use of the arrangement according to the invention in an air-conditioning system, preferably of motor vehicles, is particularly advantageous, because such air-conditioning systems operate without servicing over a period of years.

These and other features and advantages of the invention will be apparent upon consideration of the following detailed description of the preferred embodiment of the invention, taken in conjunction with the appended drawings.

DETAILED DESCRIPTION OF THE INVENTION

Figure 1:
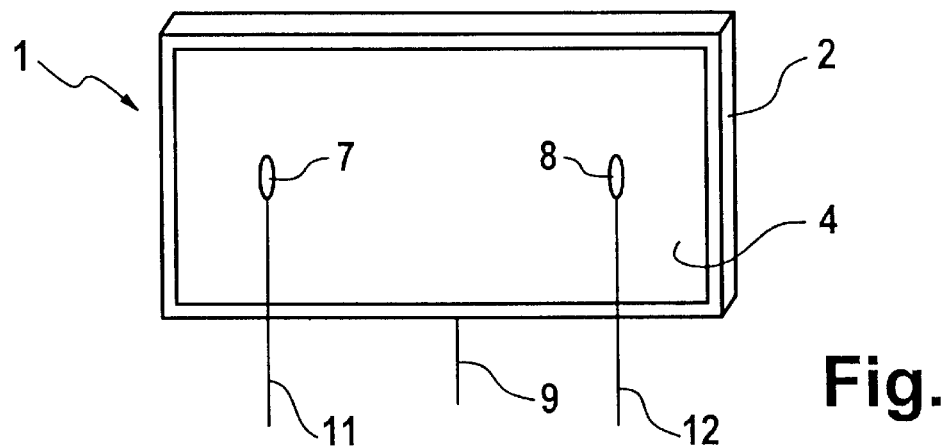
FIG. 1 shows a side view of an atmospheric humidity sensor.

While the present invention is capable of embodiment in various forms, there is shown in the drawings and will be hereinafter described a presently preferred embodiment with the understanding that the present disclosure is to be considered as an exemplification of the invention, and is not intended to limit the invention to the specific embodiment described and illustrated.

Figure 2:
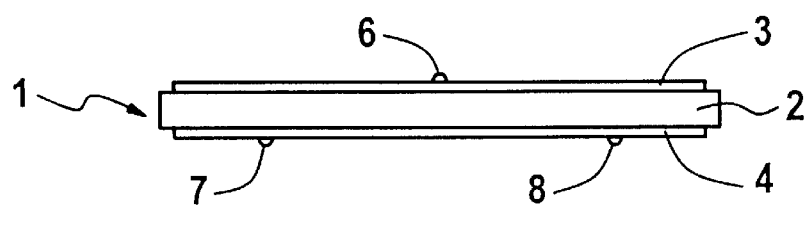
FIG. 2 shows a plan view of an atmospheric humidity sensor.

The capacitive atmospheric humidity sensor 1 represented in FIGS. 1 and 2 essentially comprises a polymer layer 2 as a dielectric and two mutually opposite electrically conductive (metallized) electrodes 3 and 4. According to another embodiment, these electrodes 3 and 4 may also lie on the dielectric 2 alongside one another. The electrodes 3 and 4 are provided with power terminals 6 and 7, 8, to which supply leads 9 and 11, 12 are connected. Since the electrode 4 is designed according to the invention as a heating resistor, two power terminals 7 and 8 are provided for temporarily supplying heating current, while the electrode 3 has only one power terminal 6. On the one hand, a heating current can be supplied via the two power terminals 7 and 8—outside the measuring periods—and on the other hand—during the measuring times—a measuring signal can at the same time be picked off via the power terminal 6.

Figure 3:
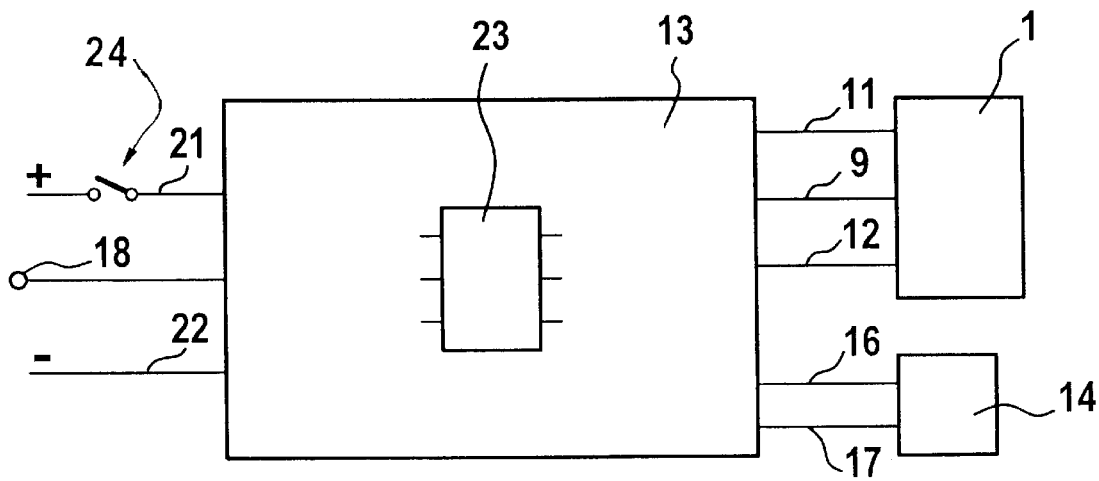
FIG. 3 shows an arrangement for the operation of an atmospheric humidity sensor and FIGS. 4a) to c) show flow diagrams of various heating cycles for the atmospheric humidity sensor.

As already stated above, the capacitive atmospheric humidity sensor 1 serves for determining relative atmospheric humidity, the supply leads 9 of the electrode 3 and 11, 12 of the electrode 4 according to FIG. 3 being connected to sensor evaluation electronics 13. Also connected to these sensor evaluation electronics 13 is a temperature sensor 14 for determining the ambient temperature via leads 16, 17. Consequently, atmospheric humidity measurement can take place in the sensor evaluation electronics 13 by measuring the capacitance of the capacitive atmospheric humidity sensor 1 and measuring the temperature by evaluating the signal supplied by the temperature sensor 14, whereby a compensating variable is generated at the same time for the determination of the exact relative atmospheric humidity.

Then the measuring signal for temperature and atmospheric humidity can be picked off at the output 18 of the sensor evaluation electronics 13 and can be displayed by means of a measuring instrument, not represented in FIG. 3. Both a current for operating the sensor evaluation electronics 13 and a heating current for the capacitive atmospheric humidity sensor 1 can be supplied via the supply leads 21, 22.

Figures 4, 4A, 4B, 4C:
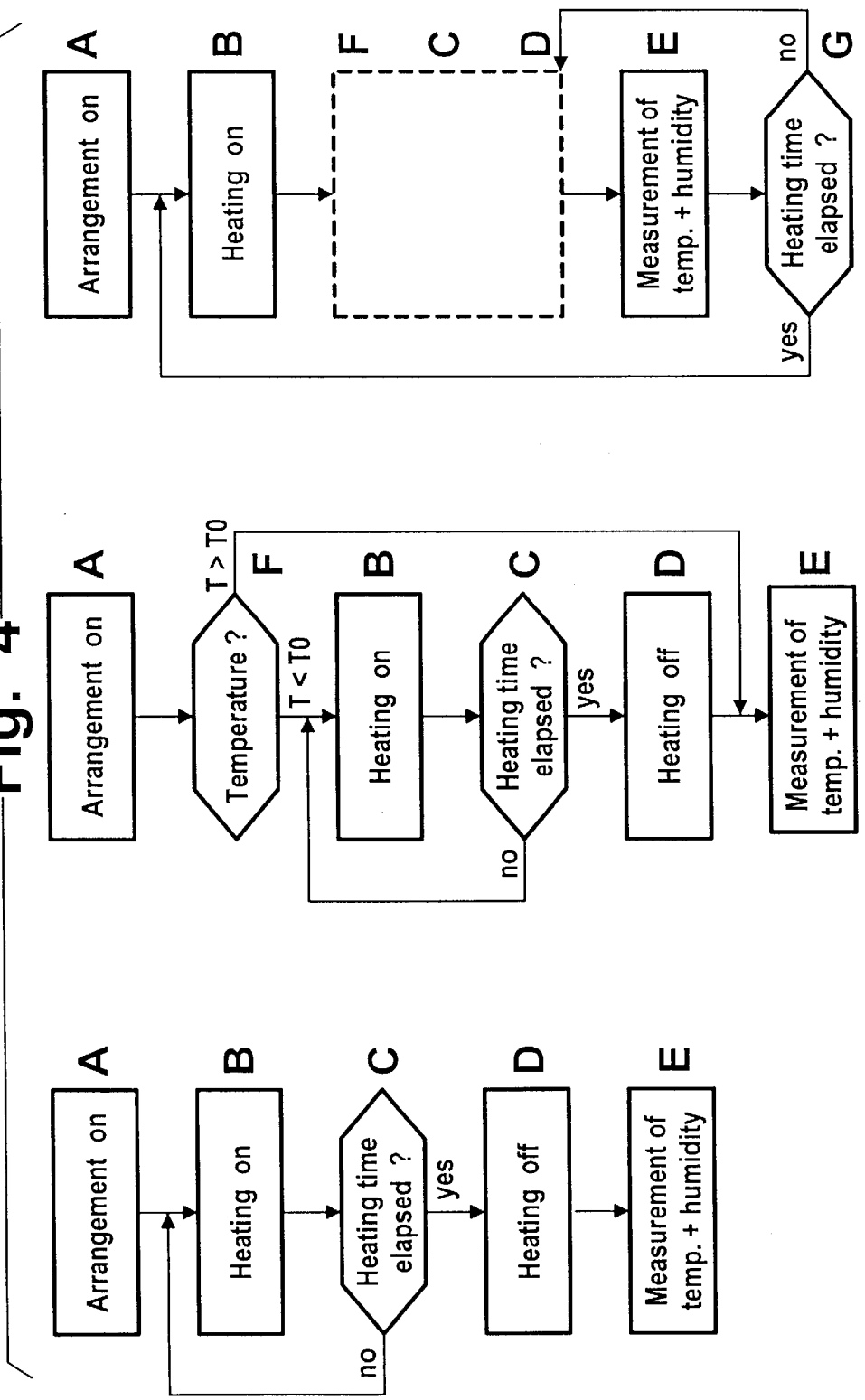

In FIG. 4, various operating modes of the arrangement according to the invention for the heating up of the capacitive atmospheric humidity sensor 1 are represented on the basis of flow diagrams according to a), b) and c). These flow diagrams may be stored, for example, as a program in a microprocessor 23 of the sensor evaluation electronics.

In the case of the flow diagram according to FIG. 4a), after the switching on (A) of the arrangement according to the invention by closing the switch 24 (in FIG. 3), the heating of the capacitive atmospheric humidity sensor 1 is at the same time switched on (B). When checking the heating time (C), either a "yes" or "no" is emitted as information, according to the duration, and the heating is interrupted (D) or continued. After the switching off of the heating, the measurement of temperature and humidity (E) then takes place.

The flow diagram according to FIG. 4b) differs from the flow diagram according to FIG. 4a) only in that, before the switching on of the heating (B), a measurement of the ambient temperature T and a comparison with a predetermined temperature value T0 (of for example +10° C.) takes place (F). Only if the ambient temperature T is below the predetermined temperature value T0 is the heating operation then initiated.

In the case of the flow diagram according to FIG. 4c), a component (G) "waiting time elapsed?" is inserted in addition to the conditions of the flow diagrams according to FIG. 4a) and FIG. 4b). In this case, the heating is only switched on when a certain waiting time (for example 10 hours) has elapsed. This may also be linked with a predetermined temperature value T0.

The foregoing description of a preferred embodiment of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined by the claims set forth below.

What is claimed is:

1. An arrangement for determining relative atmospheric humidity comprising a capacitive atmospheric humidity sensor and associated sensor evaluation electronics the capacitive atmospheric humidity sensor having a polymer layer as a dielectric and two electrically conductive electrodes wherein one of the electrically conductive, metallized electrodes is designed as a laminar heating resistor with at least two power terminals.

2. The arrangement as claimed in claim 1, wherein the electrically conductive electrodes are arranged on both sides of the polymer layer opposite one another.

3. The arrangement according to claim 1, wherein the electrically conductive electrodes are arranged on one side of the polymer layer alongside one another.

4. The arrangement as claimed in claim 1, wherein the electrically conductive electrodes consist of platinum.

5. The arrangement as claimed in claim 1, wherein the layer thickness of the electrodes is so small that they are liquid-permeable.

6. The arrangement as claimed in claim 1, wherein the heating resistor is supplied with current, and is consequently heated up, in specific time cycles.

7. The arrangement as claimed in claim 6, wherein the heating resistor is supplied with current for a short time each time the arrangement is switched on.

8. The arrangement as claimed in claim 6, wherein the heating resistor is supplied with current for a short time only when the ambient temperature is below a fixed predetermined value when the device is switched on.

9. The arrangement as claimed in claim 7, wherein the heating resistor is supplied with current in each case only after a fixed predetermined waiting time.

10. The arrangement as claimed in claim 8, wherein, for sensing the ambient temperature, there is provided a temperature sensor which is connected to the sensor evaluation electronics and emits an appropriate compensating variable for determining the exact relative atmospheric humidity by the sensor evaluation electronics.

11. The arrangement as claimed in one or more of claim 1, which comprises integration thereof in an air-conditioning system, in particular for motor vehicles.

* * * * *

UNITED STATES PATENT AND TRADEMARK OFFICE
CERTIFICATE OF CORRECTION

PATENT NO. : 6,356,087 B1 Page 1 of 1
DATED : March 12, 2002
INVENTOR(S) : Werner Wallrafen It is certified that error appears in the above-identified patent and that said Letters Patent is hereby corrected as shown below:

Column 4,
Line 55, "one or more of" should be deleted.

Signed and Sealed this

Fifth Day of November, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO.   : 6,356,087 B1  
DATED        : March 12, 2002  
INVENTOR(S)  : Werner Wallrafen It is certified that error appears in the above-identified patent and that said Letters Patent is hereby corrected as shown below:

<u>Title page,</u>
Item [22], change "1999" to -- 1998 --.

Signed and Sealed this

Seventeenth Day of December, 2002

JAMES E. ROGAN
*Director of the United States Patent and Trademark Office*